United States Patent
Lai

(10) Patent No.: US 7,444,884 B2
(45) Date of Patent: Nov. 4, 2008

(54) TENSILE TEST METHOD

(75) Inventor: Yi-Shao Lai, Taipei County (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 0 days.

(21) Appl. No.: 11/779,896

(22) Filed: Jul. 19, 2007

(65) Prior Publication Data

US 2008/0011097 A1    Jan. 17, 2008

Related U.S. Application Data

(63) Continuation of application No. 11/162,402, filed on Sep. 8, 2005, now abandoned.

(30) Foreign Application Priority Data

Dec. 6, 2004    (TW) .............. 93137586 A

(51) Int. Cl.
*G01N 3/08* (2006.01)
(52) U.S. Cl. .......................... 73/826; 73/856
(58) Field of Classification Search ............... 73/826, 73/856
See application file for complete search history.

(56) References Cited

U.S. PATENT DOCUMENTS

| 4,475,403 | A | * | 10/1984 | Lentz ........................... 73/798 |
| 4,841,779 | A | * | 6/1989 | Mitsuhashi et al. ........... 73/826 |
| 5,286,108 | A | * | 2/1994 | Whatley et al. ............... 374/49 |
| 5,515,294 | A | * | 5/1996 | Mohr et al. .................. 702/113 |
| 6,041,660 | A | * | 3/2000 | Fujitaka et al. ............... 73/826 |

\* cited by examiner

*Primary Examiner*—Max Noori
(74) *Attorney, Agent, or Firm*—Jianq Chyun IP Office

(57) ABSTRACT

A tensile test fixture and a tensile test method are provided. The tensile test fixture suits to perform a tensile test for a specimen. The tensile test fixture includes a base, a pull bar and a forcing member. The pull bar includes a limiting member, a specimen-fixing member and a shaft member. Wherein, the shaft member is connected between the position limiting member and the specimen-fixing member, and the specimen is fixed between the base and the specimen-fixing member. Otherwise, the forcing member has a cavity, which includes an opening. The shaft member passes through the opening, and the position limiting member is located in the cavity. The dimension of the limiting member is larger than the dimension of the opening so that the limiting member is restricted within the cavity. The forcing member is adopted to pull the limiting member to perform a tensile test for the specimen.

1 Claim, 4 Drawing Sheets

TENSILE TEST METHOD

CROSS-REFERENCE TO RELATED APPLICATION

This application is a continuation application of patent application Ser. No. 11/162,402, filed on Sep. 8, 2005, which claims the priority benefit of Taiwan application serial no. 93137586, filed on Dec. 6, 2004. The entirety of the above-mentioned patent applications is hereby incorporated by reference and made a part of this specification.

BACKGROUND OF THE INVENTION

1. Field of Invention

The present invention relates to a test fixture and a test method. More particularly, the present invention relates to a tensile test fixture and a tensile test method.

2. Prior Art

Along with the continual development of electronic technology, new generation electronic products with more complex functions and more human factors came forth and replaced old generations at all the times. Generally, for electronic products, after a packaging process has been finished, final product tests such as aging test, electric characteristics test, tensile test and solder ball impact test etc. need to be performed to ensure quality and yield of electronic products. Normally, for understanding that the material will be destroyed under which kind of conditions, the most primary index is material strength. There are many methods to obtain the material strength, one of the more simple methods thereof is tensile test, a stress-strain diagram can be drawn according to the test results, and a relationship of tensile stress and tensile strain can be obtained. The relationship can be used as a reference of engineering application and material characteristics evaluation by the stress-strain diagram.

Referring to FIG. 1, it is a cross-sectional view, schematically illustrating partial section plane of a conventional tensile test fixture. The conventional tensile test fixture 100 is suitable for performing a tensile test for a specimen 130. The tensile test fixture 100 includes a pull bar 110 and a base 120. When a tensile test is needed to perform on the specimen 130, a conventional method is that the specimen 130 is adhered to a place between the pull bar 110 and the bottom base 120. Then, the pull bar 110 moves along direction A by a pull mechanism (not shown) fixed in the pull bar 110, the specimen 130 fixed between the pull bar 110 and the base 120 is stretched, and the tensile test stops after the specimen is completely broken. The maximum tensile stress is found out from the measured tensile data.

However, during aforesaid conventional tensile test, the pull bar 110 of the tensile test fixture 100 starts to stretch the specimen 130 by a zero initial speed and cannot accelerate up in a short time to perform the tensile test at high speed. In another words, the conventional tensile test fixture 100 cannot study the material characteristics of the specimen 130 under a perpendicular high-speed tensile stress.

SUMMARY OF THE INVENTION

Accordingly, the present invention is to provide a tensile test fixture suited to measure the material characteristics of a specimen under high speed tensile stress.

In order to achieve aforesaid purpose, the present invention provides a tensile test fixture, suitable for performing a tensile test for a specimen. The tensile test fixture includes a base, a pull bar and a forcing member, wherein the pull bar thereof includes a position limiting member, a specimen-fixing member and a shaft member. Aforesaid shaft member is connected between the limiting member and the specimen-fixing member, and the specimen is fixed between the base and the specimen-fixing member. Moreover, the forcing member has a cavity and an opening connecting with the cavity. The shaft member passes through the opening, and the position limiting member is located in the cavity. The dimension of the position limiting member is larger than the dimension of the opening so that the position limiting member is restricted within the cavity. The forcing member can pull the limiting member of the pull bar to perform a tensile test for the specimen.

According to a tensile test fixture described in a preferred embodiment of this invention, wherein the forcing member further has a locking hole, the forcing member is adopted to fix the fastener into the locking hole, and the forcing member is connected to a pull providing mechanism by the fastener.

In order to achieve aforesaid purpose of the present invention, this invention provides a tensile test method, including fixing a specimen between the base and the specimen-fixing member of the tensile test fixture, then pulling the forcing member, letting the forcing member contact the limiting member with a speed, stretching the specimen between the base and the specimen-fixing member, wherein, aforesaid speed is larger than zero.

In order to achieve aforesaid purpose of the present invention, this invention provides a tensile test method, including fixing a specimen between a base and a pulling member, pulling the pulling member with an initial speed larger than zero to stretch the specimen between the base and the pulling member.

According to above description, the tensile test fixture of this invention performs a tensile test with an initial speed larger than zero. Thus, the tensile test fixture can perform tensile tests with different tensile initial speeds corresponding to different kinds of specimens or different actual application environments.

It is to be understood that both the foregoing general description and the following detailed description are exemplary, and are intended to provide further explanation of the invention as claimed.

BRIEF DESCRIPTION OF THE DRAWINGS

In order to the make the aforementioned and other objects, features and advantages of the present invention comprehensible, a preferred embodiment accompanied with figures is described in detail below.

DESCRIPTION OF EMBODIMENTS

Figure 1:
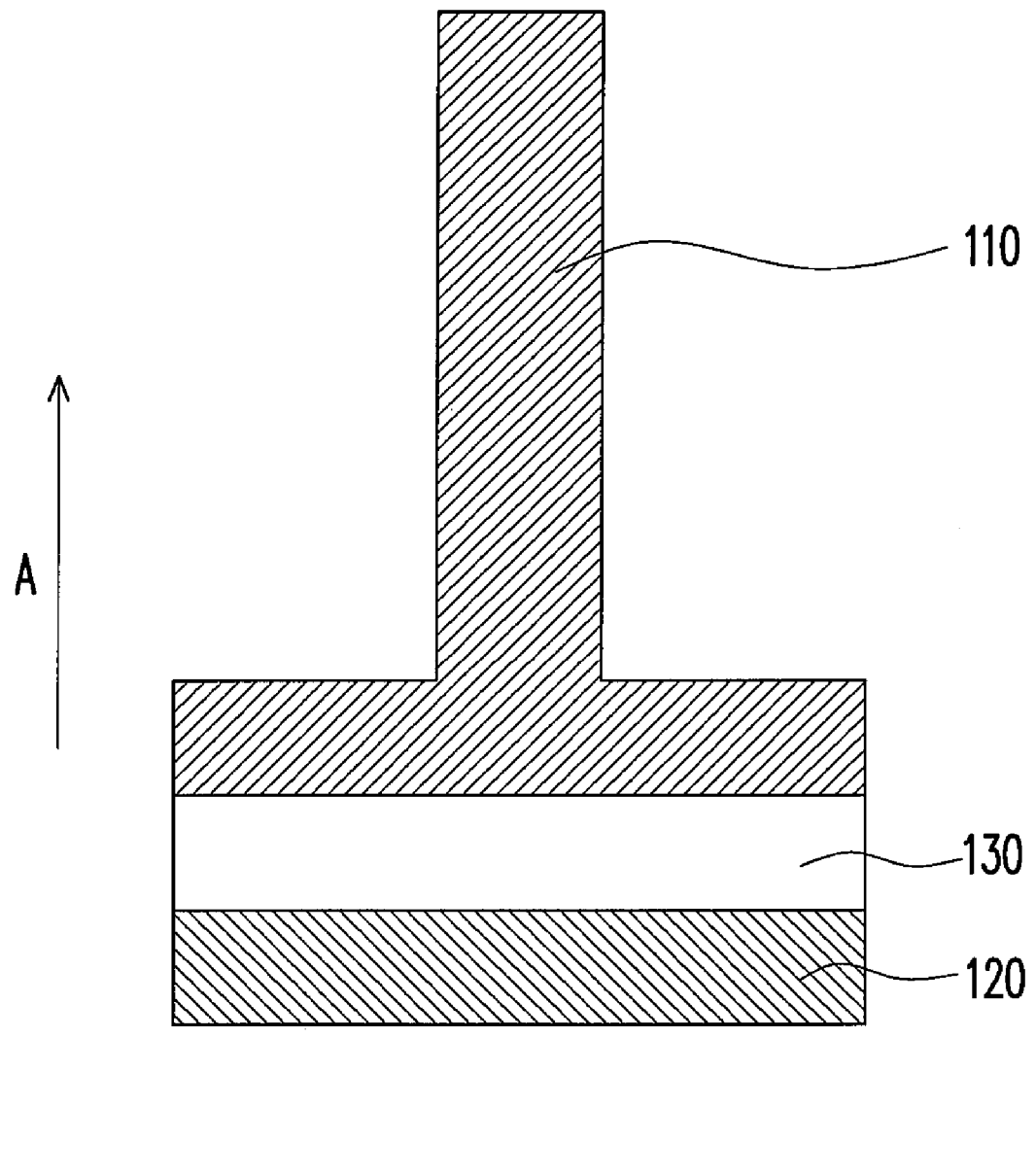
FIG. 1 is a drawing, schematically illustrating a local cross-sectional view of a conventional tensile test fixture.
Figure 2:
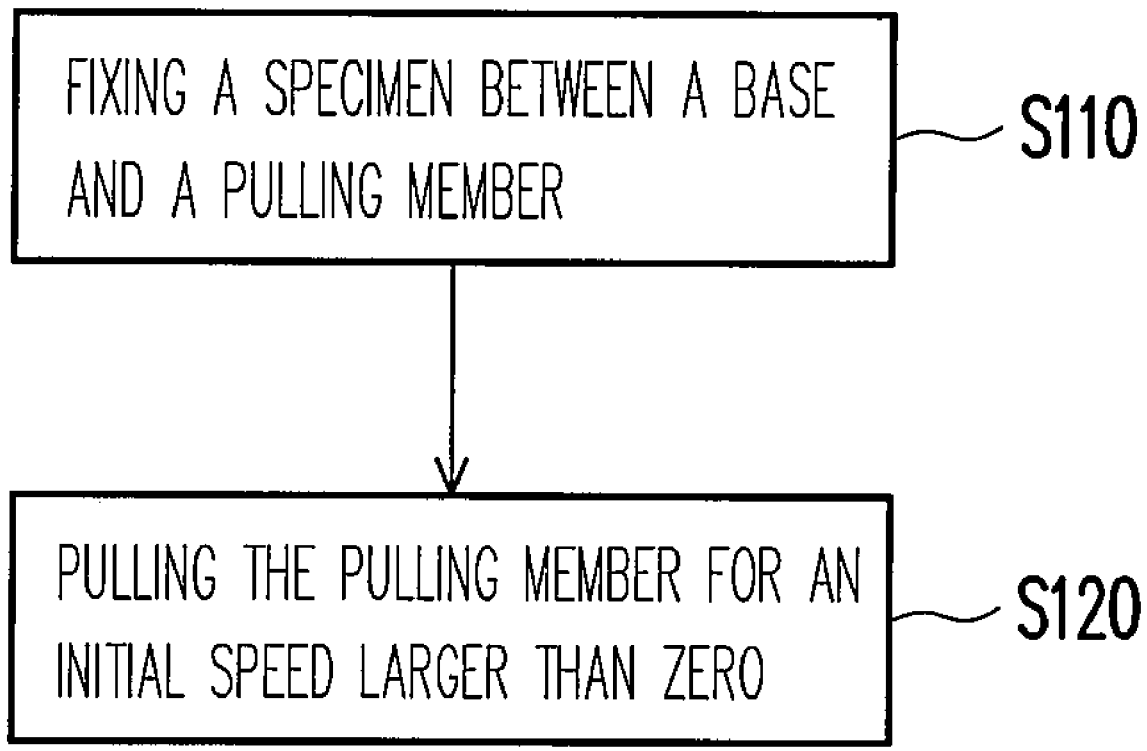
FIG. 2 is a process chart, schematically illustrating a tensile test method, according to a first embodiment of the invention.
Figure 3A:
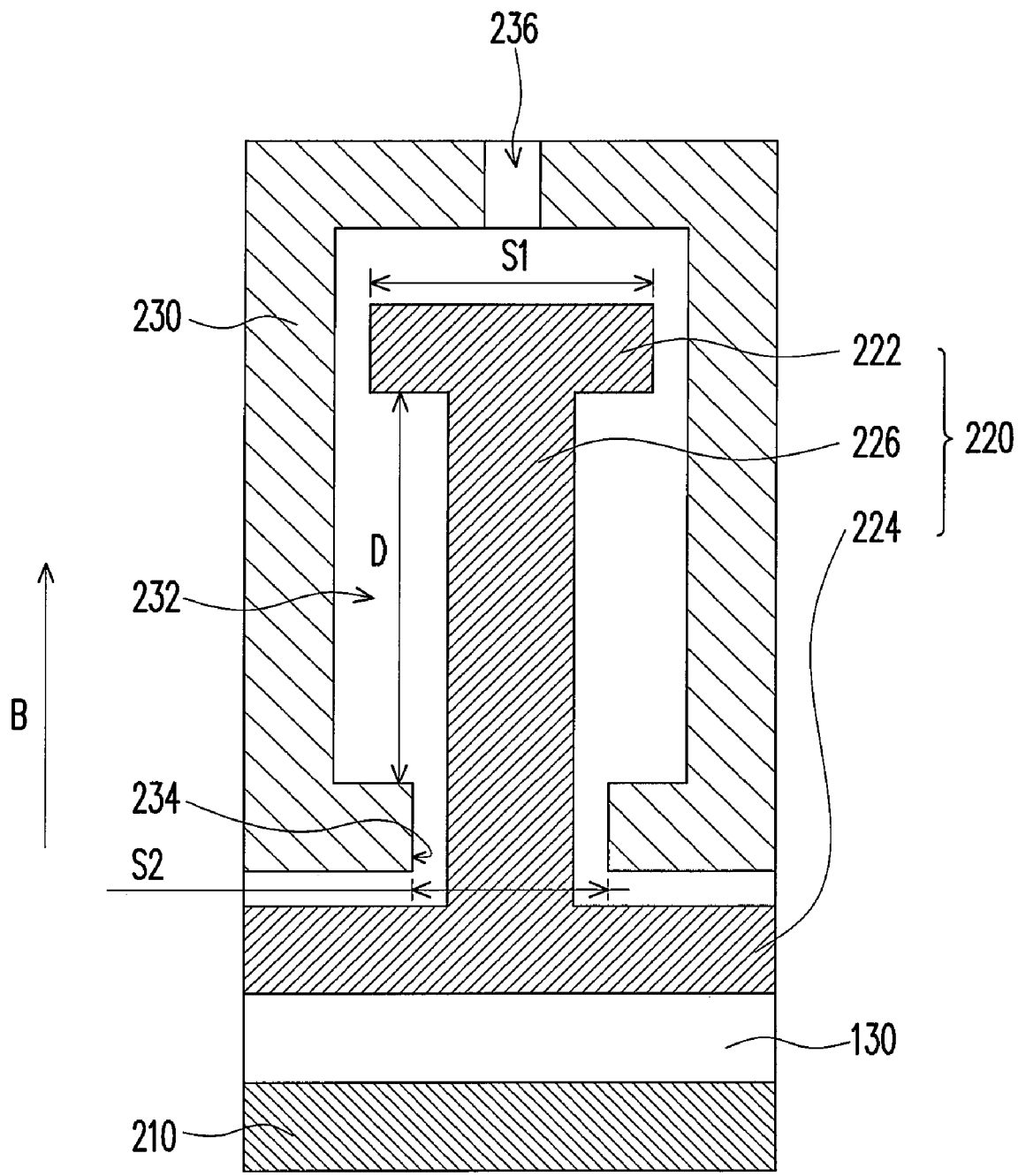
FIG. 3A is a cross-sectional view, schematically illustrating the tensile test fixture, according a preferred embodiment of the invention.

Referring to FIGS. 2 and 3A simultaneously, wherein FIG. 2 is a process chart, schematically illustrating a tensile test method, according to a first embodiment of the invention, and FIG. 3A is a cross-sectional view, schematically illustrating the tensile test fixture, according a preferred embodiment of the invention. The tensile test method in the embodiment is, fixing a specimen 130 between a base 210 and a pulling member (for example, the assembly which includes a pull bar 220 and a forcing member 230, but not limited in this design), in step S110. Wherein, for example, the method of fixing the specimen 130 between the base 210 and the pulling member is using fixing method of pasting glue in the two sides of the specimen 130, or adopting a proper clamping device etc. Furthermore, for example, aforesaid pulling member is, for example, a pull providing mechanism (not shown) connected to air pressure, oil pressure or other kind of mechanism, then, the pull providing mechanism drives the pulling member, and lets the pulling member stretch the specimen 130 between the base 210 and the pulling member with an initial speed larger than zero, in step S120. Because the initial speed of stretching the specimen 130 can be larger than zero, and the initial speed can be adjusted to high speed under test requirement, the material characteristics of the specimen 130 under high speed tensile stress can be obtained by this tensile test method.

It is noticeable that the spirit of this tensile test method in this embodiment is to perform a tensile test for the specimen 130 with an initial speed larger than zero, but not limited in using the tensile test fixture 200, any kind of tensile test fixture can be used to perform the tensile test method in this embodiment. It only needs to have the initial speed larger than zero, and then, the tensile test of the present invention can be performed.

Figure 3B:
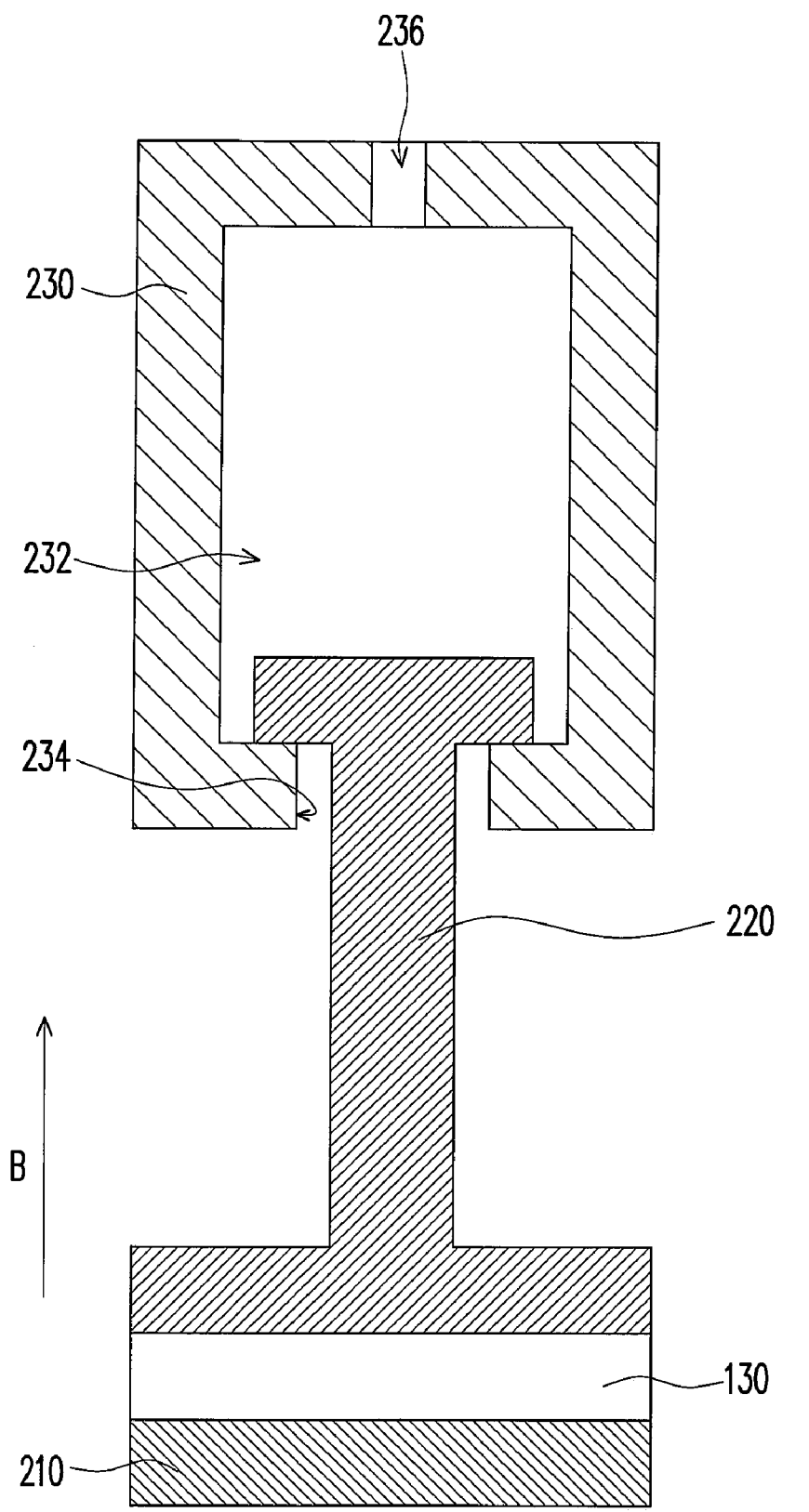
FIG. 3B is cross-sectional view, schematically illustrating the operation of the tensile test fixture in FIG. 3A.

Referring to FIGS. 3A and 3B simultaneously, wherein, FIG. 3B is cross-sectional view, schematically illustrating the operation of the tensile test fixture in FIG. 3A. The tensile test fixture 200 is adopted to perform a tensile test for a specimen 130, this tensile test fixture 200 includes a base 210, a pull bar 220 and a forcing member 230, wherein the pull bar 220 includes a position limiting member 222, a specimen-fixing member 224 and a shaft member 226. The specimen 130 is adopted to be fixed between the base 210 and the specimen-fixing member 224. In addition, the pull bar 220 can be an integrated formation or assembled by components.

Furthermore, aforesaid forcing member 230 has a cavity 232 and an opening 234 connected to the cavity 232, wherein the shaft member 226 passes through the opening 234, and the position limiting member 222 is located in the cavity 232. Because the dimension S1 of the position limiting member 222 is larger than the dimension S2 of the opening 234 so that the pull bar 220 cannot be separated from the cavity 232. In addition, the forcing member 230 is, for example, connected to a pull providing mechanism (not shown), the pull providing mechanism is, for example, coupled to air pressure, oil pressure or other appropriate design, the pull providing mechanism is adopted to drive the forcing member 230 to move along a moving direction B.

Moreover, in another preferred embodiment of this invention, the forcing member 230 has, for example, a locking hole 236 and a fastener (not shown), wherein there are threads in the inner wall of the locking hole 236, and the fastener can be fixed in the locking hole via the threads inside the locking hole. Then, the forcing member 230 is connected to the pull providing mechanism via the fastener.

Referring to FIGS. 3A and 3B again, a tensile test method in the second embodiment of this invention will be introduced hereinafter. The tensile test method performs a test by using the tensile test fixture. First, the specimen 130 is fixed between the base 210 and the specimen-fixing member 224. Then, the forcing member 230 moves along the moving direction B, driven by the pulling proving mechanism. It is noticeable that the forcing member 230 moves along the moving direction B by a distance D (as shown FIG. 3A) before the forcing member 230 contacts the position limiting member 222 of the pull bar 220, and the speed of the forcing member 230 can increase gradually during the moving period till the speed meets a speed set by a measurement person. In another words, the forcing member 230 can be accelerated to the speed set by the measurement person from the beginning (static status). When the forcing member 230 contacts the position limiting member 222 of the pull bar 220, the forcing member 230 starts to stretch the specimen 130 fixed between the pull bar 220 and the base 210 via the pull bar 220. A stress-strain diagram for the specimen 130 can be obtained during the procedure of performing the tensile test on the specimen 130. When a complete fracture occurs on the specimen 130, the tensile test stops. Here, the measurement person can get the maximum tensile stress by which the specimen 130 can tolerate, and the various material characteristics from aforesaid stress-strain diagram.

In conclusions, the tensile test fixture of this invention performs a tensile test for the specimen with an initial speed larger than zero, and the initial speed can be adjusted to a high speed according to test requirement. Thus, the tensile test fixture can be used to perform tensile tests with different tensile initial speed corresponding to different kinds of specimens or different actual application environments. The material characteristics of the specimen under high speed tensile stress can be obtained.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A tensile test method, suitable for performing a tensile test on a specimen by a tensile test fixture, wherein the tensile test fixture comprises:
    a base;
    a pull bar, comprising a position limiting member, a specimen-fixing member and a shaft member, wherein the shaft member is connected between the position limiting member and the specimen-fixing member, wherein the specimen is adopted to be fixed between the -base and the specimen-fixing member; and
    a forcing member, having a cavity and an opening connected with the cavity, wherein the shaft member passes through the opening, and the position limiting member is located within the cavity, a dimension of the position limiting member is larger than a dimension of the opening so that the position limiting member is not separated from the cavity, the forcing member is adopted to pull the position limiting member of the pull bar to perform a tensile test for the specimen, the tensile test method comprising
    fixing a specimen between the base and the specimen-fixing member of the tensile test fixture; and
    pulling the forcing member to allow the forcing member to contact the position limiting member with a speed, and stretching the specimen between the base and the specimen-fixing member, wherein the speed is larger than zero.

* * * * *